US006534655B1

(12) United States Patent
Arnold et al.

(10) Patent No.: US 6,534,655 B1
(45) Date of Patent: Mar. 18, 2003

(54) INDENO[1,2-C]PYRAZOLE DERIVATIVES FOR INHIBITING TYROSINE KINASE ACTIVITY

(75) Inventors: Lee D. Arnold, Westborough, MA (US); Yajun Xu, Westborough, MA (US); Teresa Barlozzari, Wellesley, MA (US); Paul Rafferty, Nottingham (GB); Michael Hockley, Nottingham (GB); Allyson Turner, Nottingham (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/541,309

(22) Filed: Apr. 3, 2000

Related U.S. Application Data

(63) Continuation of application No. PCT/US98/21259, filed on Oct. 6, 1998.

(60) Provisional application No. 60/061,142, filed on Oct. 6, 1997.

(51) Int. Cl.[7] .................. C07D 401/04; A61K 31/4155; A61K 31/4439

(52) U.S. Cl. .................... 546/275.7; 514/338; 514/339; 546/275.7; 548/359.1

(58) Field of Search ................................ 514/338, 339; 546/275.7; 548/359.1

(56) References Cited

U.S. PATENT DOCUMENTS

| | | | | |
|---|---|---|---|---|
| 3,843,665 A | | 10/1974 | Coombs et al. | 546/275.7 |
| 3,932,430 A | * | 1/1976 | Habeck et al. | 546/275.7 |
| 5,593,997 A | | 1/1997 | Dow et al. | 514/258 |

FOREIGN PATENT DOCUMENTS

| | | |
|---|---|---|
| JP | 58240686 | 7/1985 |
| WO | WO 92/20642 | 11/1992 |
| WO | WO 94/14777 | 7/1994 |
| WO | WO 96/14843 | 5/1996 |
| WO | WO 96/31510 | 10/1996 |

OTHER PUBLICATIONS

El–Rayyes, N.R., et al., et al., "Heterocycles. Part XVII. Synthesis of New Substituted 2,3,3a,4,5,6–Hexahydrobenzo [6,7] cyclohepta [1,2–c] pyrazoles and Related Compounds," *J. Heterocyclic Chem.*, 26:209–214 (1989).

Yoshimura, H., et al., "A Novel Type of Retinoic Acid Receptor Antagonist: Synthesis and Structure–Activity Relationships of Heterocyclic Ring–Containing Benzoic Acid Derivatives," *J. Med. Chem.*, 38:3163–3173 (1995).

Palmer, B.D., et al., "Tyrosine Kinase Inhibitors. 11. Soluble Analogues of Pyrrolo– and Pyrazoloquinazolines as Epidermal Growth Factor Receptor Inhibitors: Synthesis, Biological Evaluation, and Modeling of the Mode of Binding," *J. Med. Chem.* 40:1519–1529 (1997).

* cited by examiner

*Primary Examiner*—Alan L. Rotman
*Assistant Examiner*—Janet Coppins
(74) *Attorney, Agent, or Firm*—Gayle B. O'Brien

(57) ABSTRACT

Chemical compounds that are derivatives of indeno[1,2-c] pyrazole are inhibitors of tyrosine kinase activity. Several of the tyrosine kinases, whose activity is inhibited by these chemical compounds, are involved in angiogenic processes. Thus, these chemical compounds can ameliorate disease states where angiogenesis or endothelial cell proliferation is a factor. Compounds of this invention also inhibit the induction of vascular hyperpermeability and the associated formation of edema, ascites, and exudates.

11 Claims, No Drawings

INDENO[1,2-C]PYRAZOLE DERIVATIVES FOR INHIBITING TYROSINE KINASE ACTIVITY

RELATED APPLICATIONS

This application is a continuation of International Application No. PCT/US98/21259 filed on Oct. 6, 1998 which claims the benefit of U.S. Provisional Application No. 60/061,142, filed Oct. 6, 1997 the entire teachings of which are incorporated herein by reference.

BACKGROUND OF THE INVENTION

Protein tyrosine kinases (PTKs) comprise a large and diverse class of proteins having enzymatic activity. The PTKs play an important role in the control of cell growth and differentiation (for review, see Schlessinger & Ullrich, 1992, *Neuron* 9:383–391).

For example, receptor tyrosine kinase mediated signal transduction is initiated by extracellular interaction with a specific growth factor (ligand), typically followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signalling molecules that facilitate the appropriate cellular response. (e.g., cell division, metabolic effects, responses to the extracellular microenvironment) see Schlessinger and Ullrich, 1992, *Neuron* 9:1–20.

With respect to receptor tyrosine kinases, it has been shown also that tyrosine phosphorylation sites function as high-affinity binding sites for SH2 (src homology) domains of signaling molecules (Fantl et al., 1992, *Cell* 69:413–423; Songyang et al., 1994, *Mol. Cell. Biol.* 14:2777–2785; Songyang et al., 1993, *Cell* 72:767–778; and Koch et al., 1991, *Science* 252:668–678). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767–778). The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles (Songyang et al., 1993, *Cell* 72:767–778). These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signalling pathways recruited by specific growth factor receptors, as well as differentiation factor receptors.

Aberrant stimulation, expression or mutations in the PTKs have been shown to lead to either uncontrolled cell proliferation (e.g., malignant tumor growth) or to defects in key developmental or reparative processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212).

At present, at least nineteen (19) distinct RTK subfamilies have been identified. One RTK subfamily, designated the HER subfamily, is believed to be comprised of EGFR, HER2, HER3, and HER4. Ligands to the HER subfamily of receptors include epithelial growth factor (EGF), TGF-$\alpha$, amphiregulin, HB-EGF, betacellulin and heregulin. Aberrant regulation of HER2/erbB2 kinase activity is believed to promote a transformed tumorigenic phenotype especially in breast carcinomas. Two other RTK subfamilies are designated the insulin receptor subfamily, which is comprised of INS-R, IGF-1R and IR-R, and "PDGFR" subfamily which includes the PDGF$\alpha$ and $\beta$-receptors, CSF-1R, and c-kit.

Several receptor tyrosine kinases, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as fetal liver kinase 1 (flk-1), is a member of the type III subclass of RTKs. An alternative designation for human flk-1 is kinase insert domain-containing receptor (KDR) (Terman et al., *Oncogene* 6:1677–83, 1991). Another alternative designation for flk-1/KDR is "vascular endothelial cell growth factor receptor 2" (VEGFR-2). The murine version of flk-1/VEGFR-2 has also been called NYK (Oelrichs et al, *Oncogene* 8 (1):11–15, 1993). DNAs encoding mouse, rat and human flk-1 have been isolated, and the nucleotide and encoded amino acid sequences reported (Matthews et al., *Proc. Natl. Acad. Sci. USA*, 88:9026–30, 1991; Terman et al., 1991, supra; Terman et al., *Biochem. Biophys. Res. Comm.* 187:1579–86, 1992; Sarzani et al., supra; and Millauer et al., *Cell* 72:835–846, 1993).

The type III subclass RTK designated fms-like tyrosine kinase-1 (flt-1) is related to flk-1/KDR (DeVries et al. *Science* 255;989–991, 1992; Shibuya et al., *Oncogene* 5:519–524, 1990). An alternative designation for flt-1 is "vascular endothelial cell growth factor receptor 1" (VEGFR-1). To date, members of the flk-1/KDR/VEGFR-2 and flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine & Growth Factor Reviews* 7: 259–270, 1996). Flt-1 is believed to be essential for endothelial organization during vascular development. Flt-1 expression is associated with early vascular development in mouse embryos, and with neovascularization during wound healing (Mustonen and Alitalo, supra). Expression of flt-1 in adult. organs suggests an additional function for this receptor that is not related to cell growth (Mustonen and Alitalo, supra).

Another RTK that is related to flt-1 and flk-1/KDR is flt-4 (Galland et al., *Oncogene* 8:1233–40, 1993; Pajusola et al., *Oncogene* 8:2931–37, 1993). Features shared by these three receptors include the seven immunoglobulin-like domains in their extracellular region. The amino acid sequence of flt-4 exhibits significant homology with the sequences of flt-1 and flk-1, especially in the tyrosine kinase domain (Galland et al., supra). Unlike flt-1 and flk-1/KDR, however, a precursor form of flt-4 is cleaved during post-translational processing to form two disulfide-linked polypeptides (Pajusola et al., supra). Studies of flt-4 expression during development support the theory of venous origin of lymphatic vessels (Kaipainen et al., *Proc. Natl. Acad. Sci. USA* 92:3566–70, April, 1995).

Given the crucial role of endothelial cells in angiogenesis, growth factors that act on endothelial cells are of particular interest for studies of the regulation of vascularization. One such factor is vascular endothelial cell growth factor (VEGF), which binds to both Flk-1 and Flt-1 with relatively high affinity and is mitogenic toward vascular endothelial cells (Terman et al., 1992, supra; Mustonen et al. supra; DeVries et al., supra). VEGF does not bind to flt-4 (Pajusola et al., supra). The studies reported in Millauer et al., supra, suggest that VEGF and flk-1/KDR/VEGFR-2 are a ligand-receptor pair that play an important role in the formation and sprouting of blood vessels, termed vasculogenesis and angiogenesis, respectively.

Different forms of VEGF arising from alternative splicing of mRNA have been reported, including the four species described by Ferrara et al. (*J. Cell. Biochem.* 47:211–218, 1991). Both secreted and predominantly cell-associated species of VEGF were identified by Ferrara et al. supra, and the protein is known to exist in the form of disulfide linked dimers.

It is also known that there are a variety of physiological and biochemical mechanisms that underlie edema and the formation of the edematous state in an individual. An important mediator in one or more of these mechanisms is "vascular endothelial cell growth factor" (VEGF). This mediator is also known as "vascular permeability factor" (VPF). This factor upregulates transport in vascular endothelial cells, and causes an increase in the permeability of numerous vascular beds including the skin, subcutaneous tissues, peritoneal wall, mesentery, diaphragm, trachea, bronchi, duodenum and uterus. Significant diapedesis, alterations in exchange across the endothelium, extravasation and deposition of macromolecules at these sites and prolonged hypotension may accompany these increased permeability effects. These processes are thought to be a facilitating prelude to neovascularization. VEGF is expressed by inflammatory T-cells, macrophages, neutrophils and eosinophils, etc., at sites of inflammation. This factor is upregulated by hypoxia, certain vasopressor hormones, growth factors, reproductive hormones and numerous inflammatory cytokines. VEGF-mediated vascular permeability has been implicated in such disorders as tumor ascites, endometriosis, edematous responses to bums and trauma, endothelial dysfunction in diabetes, ovarian hyperstimulation syndrome complications, and ocular edema.

Thus, it is apparent that the inhibition of VEGF production or activity would be beneficial, especially to block the manifestation of the above-listed disorders. In particular, agents that are capable of blocking VEGF mediated hyperpermeability and edema and associated syndromes would be useful for alleviating these disorders.

Placenta growth factor (PIGF) has an amino acid sequence that exhibits significant homology to the VEGF sequence (Park et al., *J. Biol. Chem.* 269:25646–54, 1994; Maglione et al. *Oncogene* 8:925–31, 1993). As with VEGF, different species of PIGF arise from alternative splicing of mRNA, and the protein exists in dimeric form (Park et al., supra). PIGF binds flt-1 with high affinity, but not flk-1/KDR (Park et al., supra). PIGF potentiates the mitogenic effect of VEGF on endothelial cells when VEGF is present at low concentrations, but has no detectable effect when VEGF is present at higher concentrations (Park et al., supra).

Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al., 1994*, DN&P* 7(6):334–339, which is incorporated herein by reference.

Inhibiting angiogenesis is desirable in certain clinical situations (e.g., to suppress growth and metastasis of solid tumors, or in treating rheumatoid arthritis), whereas promotion of vascularization is beneficial for treating other conditions (e.g., wound healing). Consequently, molecules that promote angiogenesis by transducing signals through the above-discussed receptors, and molecules capable of inhibiting such signal transduction, are both of interest.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzynes has been linked to oncogenesis. A more detailed discussion of non-receptor tyrosine kinases is provided in Bolen, 1993*, Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. application Ser. No. 4,966,849), soluble receptors and antibodies (application Ser. No. WO 94/10202; Kendall & Thomas, 1994*, Proc. Natl. Acad. Sci* 90:10705–09; Kim et al., 1993*, Nature* 362:841–844), RNA ligands (Jellinek, et al., *Biochemistry* 33:10450–56; Takano, et al., 1993*, Mol. Bio. Cell* 4:358A; Kinsella, et al. 1992, Exp. *Cell Res.* 199:56–62; Wright, et al., 1992*, J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994*, Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642), and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

The identification of effective small compounds which specifically inhibit tyrosine signal transduction by modulating the activity of receptor and non-receptor tyrosine kinases to regulate and modulate abnormal or inappropriate cell proliferation is therefore desirable.

SUMMARY OF THE INVENTION

This invention is directed to compounds of the formula

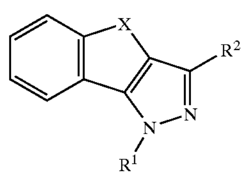

I wherein:

X is a carbonyl, a methylene or a substituted methylene group;

$R^1$ is a hydrogen or methyl group; and $R^2$ is a pyridyl, a phenyl, or a substituted phenyl;

provided that when X is a methylene group, $R^1$ is a methyl group.

Enantiomers, tautomers, and mixtures of these compounds are included in this invention. Pharmaceutically acceptable acid addition salts of these compounds are also included in this invention.

The compounds of this invention are useful as inhibitors of the tyrosine kinase activity. In particular, the compounds of this invention are useful as inhibitors of tyrosine kinases that are important in the process of angiogenesis. These compounds are also useful as inhibitors of tyrosine kinases that are important in the process of vascular hyperpermeability. Since these compounds are anti-angiogenic and inhibit vascular hyperpermeability, they are important substances for inhibiting the progression disease states where angiogenesis and vascular hyperpermeability are important components.

Particularly preferred compounds of the present invention are compounds of formula I wherein $R^1$, $R^2$ and X shown in Table I:

TABLE I

| $R^1$ | $R^2$ | X |
|---|---|---|
| H | Phenyl | CO |
| H | 4-methylphenyl | CO |
| H | 4-fluorophenyl | CO |
| H | 3-chlorophenyl | CO |
| H | 4-chlorophenyl | CO |
| H | 4-bromophenyl | CO |
| H | 4-hydroxyphenyl | CO |
| H | 3-methoxyphenyl | CO |
| H | 4-methoxyphenyl | CO |
| H | 4-hydroxy-3-methoxyphenyl | CO |
| H | 3-pyridyl | CO |
| H | 4-pyridyl | CO |
| H | 3,4-$(OCH_3)_2$ phenyl | CO |
| H | phenyl | CH(OH) |
| $CH_3$ | phenyl | CO |
| $CH_3$ | 4-methylphenyl | CO |
| $CH_3$ | 3-chlorophenyl | CO |
| $CH_3$ | 4-chlorophenyl | CO |
| $CH_3$ | 4-bromophenyl | CO |
| $CH_3$ | 4-hydroxyphenyl | CO |
| $CH_3$ | 3-methoxyphenyl | CO |
| $CH_3$ | 4-methoxyphenyl | CO |
| $CH_3$ | 4-aminophenyl | CO |
| $CH_3$ | 3-pyridyl | CO |
| $CH_3$ | 4-chlorophenyl | $CH_2$ |
| $CH_3$ | 4-methoxyphenyl | $CH_2$ |
| $CH_3$ | phenyl | CH(OH) |
| $CH_3$ | 4-chlorophenyl | CH(OH) |
| $CH_3$ | 3-pyridyl | CH(OH) |
| $CH_3$ | 4-methoxyphenyl | $CH(NH_2)$ |
| $CH_3$ | phenyl | $CH(NHC_3H_7)$ |
| $CH_3$ | phenyl | $CH(NHC_2H_4N(CH_3)_2)$ |

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases.

DETAILED DESCRIPTION OF THE INVENTION

The compounds of this invention have antiangiogenic properties. For this reason, these compounds can be used as active agents against such disease states as arthritis, atherosclerosis, psoriasis, hemangiomas, myocardial angiogenesis, coronary and cerebral collateral vascularization, ischemic limb angiogenesis, wound healing, peptic ulcer Helicobacter related diseases, fractures, cat scratch fever, rubeosis, corneal disease, neovascular glaucoma and retinopathies such as those associated with diabetic retinopathy or macular degeneration, or similar disease states dependent on angiogenesis-supported blood and nutrient supply or on endothelial cell hyperproliferative disorders. In addition, some of these compounds can be used as antifertility agents or as abortifacients.

The compounds of this invention inhibit the catalytic activity of tyrosine kinases. That is, these compounds modulate signal transduction by tyrosine kinases. In particular, these compounds selectively inhibit the activity of the KDR/FLK-1/VEGFR-2 tyrosine kinases. Certain compounds of this invention also inhibit the activity of additional tyrosine kinases such as flt-1/VEGFR-1, Src-subfamily kinases such as Lck, Src, fyn, yes, etc. The occurrence and potency of the inhibitory activity of the compounds of this invention against a particular tyrosine kinase is dependent on the nature, number and arrangement of the substituents (i.e. X, $R^1$ and $R^2$) of these compounds.

The compounds of this invention, when administered to individuals in need of such compounds, also inhibit vascular hyperpermeability and the formation of edema in these individuals. These compounds act, it is believed, by inhibiting the activity mediated by VEGF receptors which are involved in the process of vascular hyperpermeability and edema formation. VEGF is unique in that it is the only angiogenic growth factor known to directly contribute to vascular hyperpermeability and the formation of edema. Indeed, vascular hyperpermeability and edema that is associated with the expression or administration of many other growth factors appears to be mediated via VEGF production. Diapedesis also often accompanies vascular hyperpermeability. Similarly, excessive vascular hyperpermeability can disrupt normal molecular exchange across the endothelium in critical tissues and organs (e.g., lung and kidney), thereby perturbing function and causing macromolecular extravasation and deposition. By inhibiting the kinase activity of VEGF receptors, hyperpermeability, as well as associated extravasation, subsequent edema or ascites formation and matrix deposition is inhibited and minimized.

In addition, the N-methylated forms or N-methylated analogs of the compounds of this invention can also serve as prodrugs which act as metabolically activated antiangiogenic agents.

It is envisaged that the disorders listed above are mediated to a significant extent by protein tyrosine kinase activity involving the KDR/VEGFR-2 and/or the flt-1/VEGFR-1 tyrosine kinases. By inhibiting the activity of these tyrosine kinases, the progression of the listed disorders or physiological conditions is inhibited because the angiogenic component of these disease states or physiological conditions is severely curtailed. The action of the compounds of this invention, by their selectivity for specific tyrosine kinases, result in a minimization of side effects that would occur if less selective tyrosine kinase inhibitors were used.

The potency and specificity of the generic compounds of this invention can often be altered and optimized by substituent variations and conformational restrictions.

In this invention, the following definitions are applicable:

"Pharmaceutically acceptable acid addition salt" refers to those salts which retain the biological effectiveness and properties of the free bases and which are obtained by reaction with inorganic acids such as hydrochloric acid, hydrobromic acid, sulfuric acid, nitric acid, phosphoric acid or with organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

In the compounds of this invention, the substituents of $R^2$, when $R^2$ is a phenyl, can be a lower alkyl of 1 or 2 carbon atoms, a halogen atom, a lower alkoxy group, a hydroxyl group or an amino group. In the compounds of this invention, X can be a carbonyl group, a methylene group, a hydroxymethylene group, an amino methylene group or a lower alkyl amino methylene group.

Pharmaceutical Formulations and Routes of Administration

The identified compounds of this invention can be administered to a human patient by themselves or in pharmaceutical compositions where they are mixed with suitable carriers or excipient(s) at doses to treat or ameliorate a variety of disorders. A therapeutically effective dose further refers to that amount of the compound sufficient to result in amelioration of symptoms. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than a systemic manner, for example, via injection of the compound intra-articularly (e.g., for rheumatoid arthritis), often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g. bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the PTK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cellular assays. For example, a dose can be formulated in animal models to achieve a circulating concentration range that includes the $IC_{50}$ as determined in cellular assays (i.e., the concentration of the test compound which achieves a half-maximal inhibition of the PTK activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of a cellular hyperproliferative disorder, inhibition of angiogenesis, treatment of fibrosis, diabetes, edema, ascites and the like.

EXEMPLIFICATIONS

I. Synthesis of Compounds

The compounds of this invention, formula I, can be synthesized by using the following scheme.

Synthesis of Indeno[1,2-c]pyrazole Ring System:

The indeno[1,2-c]pyrazole ring system can be synthesized by the methods of Braun and Mosher (Braun, R. A.; Mosher, W. A. *J. Am. Chem. Soc.* 1958, 80, 4919 and Braun, R. A.; Mosher, W. A. *J. Org. Chem.* 1959, 24, 648) by reacting the appropriately acylated 1,3-indandione with hydrazine or methylhydrazine.

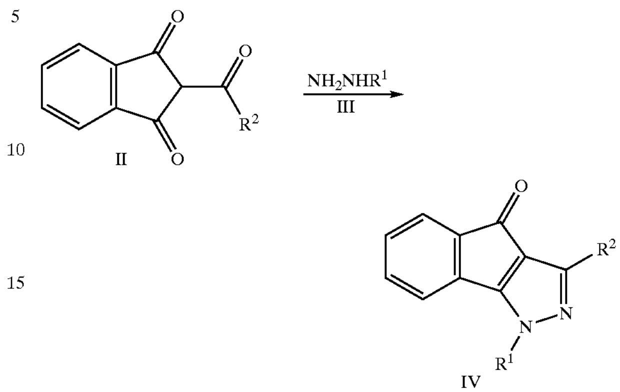

Functionalization of the Bridging Carbon:

The bridging carbonyl can be transformed to a methylene group via a Wolf-Kishner reduction of the corresponding hydrazone (Mosher, W. A., Tawfik, E.-Z., Lipp, D. W. *J. Org. Chem.* 1971, 36, 3890).

Additional methods for functionalization of the bridging carbonyl and specific examples can be found in Japanese Patent Application JP 60 130521 A2, and B. Loev, U.S. Pat. No. 3,004,983 (1960).

EXAMPLES

The invention is further illustrated by the following Examples which are given by way of example only. The final product of each of these Examples was characterized by one or more of the following procedures: high performance liquid chromatography; elemental analysis, nuclear magnetic resonance spectroscopy, infrared spectroscopy and high resolution mass spectroscopy. The following abbreviations are used:

DMF=dimethylformamide;

IMS=industrial methylated spirits; and

LCMS=liquid chromatography/mass spectroscopy

Examples 1 and 2 were prepared by methods outlined in JP60-130521.

Example 1

3-(3,4-Dimethoxyphenyl)indeno[1,2-c]pyrazol-4(1H)-one, (Commercially Available from Menai Organics Ltd., Unit 5, Menai Technology Centre Deiniol Road, Bangor Gwynedd, N. Wales LL57 2UP UK.)

Example 2

3-(3,4,5-Trimethoxyphenyl)indeno[1,2-c]pyrazol-4(1H)-one, m.p.268–272° C.

Example 3 a) Dimethyl phthalate (15.0 g) in tetrahydrofuran (100 ml) was added to a stirred suspension of sodium methoxide (8.31 g) in tetrahydrofuran (60 ml) followed by 4'-chloroacetophenone (11.8 g) in tetrahydrofuran (100 ml) at 20° C. under nitrogen. The mixture was then boiled under reflux for 18 hours then cooled to 20° C. and poured into ether (250 ml) and water (250 ml). The aqueous layer was separated and the organic layer was washed with water (3×75 ml). The combined aqueous extract and washings were acidified with concentrated hydrochloric acid and the solid which precipitated was collected by filtration. The filtrate was extracted with dichloromethane, dried and evaporated. The residue was recrystallized from ethanol to give 2-(4-chlorobenzoyl)-indan-1,3-dione.

b) The product from a) (1.23 g) was suspended in ethanol (40 ml) and hydrazine hydrate (0.216 g) was added under nitrogen. The mixture was boiled under reflux under nitrogen for 4 hours, then allowed to cool to ambient temperature and left standing for 16 hours, then filtered to give 3-(4-chlorophenyl)indeno[1,2-c]pyrazol-4(1H)-one, m.p. >330° C.

Example 4

3-(4-Chlorophenyl)indeno[1,2-c]pyrazol-4(1H)-one (0.68 g) was dissolved in N,N-dimethylformamide (30 ml) under nitrogen at 20° C. Sodium hydride (106 mg, of a 60% dispersion in mineral oil) was added and the mixture was stirred for 30 minutes, then iodomethane (0.38 g) was added. The mixture was stirred at 20° C. for 2 hours and then poured into water (50 ml). A yellow solid was collected by filtration and washed with petroleum ether (25 ml). The solid was dissolved in hot ethyl acetate and pre-absorbed onto silica which was applied to the top of the silica column. The mixture was separated by flash column chromatography using dichloromethane/petroleum ether/methanol (50:50:1). Fractions were collected, combined as appropriate, and evaporated to give a solid which was crystallised from ethyl acetate to give 3-(4-chlorophenyl)-1-methylindeno [1,2-c] pyrazol-4(1H-one, m.p. 219–221° C. $\delta_H[^2H_6]$ DMSO (250 MHz) 4.07 (3H, s, NMe), 7.41 (1H, t, Ar), 7.55 (4H, m, Ar), 7.65 (1H, d, Ar-8-H), 8.13 (2H, d, Ar). The structure was identified by the presence of a Nuclear Overhauser Effect.

Example 5 a) In a similar manner to Example 4, 3-phenylindeno[1,2-c]pyrazol-4(1H)-one (1.0 g) was reacted with iodomethane (0.64 g) at 20° C. to give, after separation by flash column chromatography, 1-methyl-3-phenylindeno[1,2-c]pyrazol-4(2H)-one, m.p. 187–188° C.

Example 6

A mixture of 3-(3,4-dimethoxyphenyl)indeno[1,2-c] pyrazol-4(1H)-one (0.6 g) and sodium borohydride (0.16 g) in absolute ethanol (100 ml) was boiled under reflux for 5 hours. The reaction mixture was cooled and the ethanol removed under reduced pressure. Water (20 ml) was added and the mixture was extracted with ethyl acetate (3×50 ml). The combined ethyl acetate extracts were washed with water, dried, filtered and evaporated to give a solid which was purified by preparative high performance liquid chromatography on a Dynamax C18 reverse phase (41.4×250 mm) column using acetonitrile/triethylammonium formate buffer as eluant to give 3-(3,4-dimethoxyphenyl)-1,4-dihydroindeno[1,2-c]pyrazol-4-ol, m.p. 197–199° C.

Example 7

A mixture of 3-phenylindeno[1,2-c]pyrazol-4(1H)-one (0.86 g), sodium borohydride (0.26 g) and absolute ethanol (200 ml) was stirred at ambient temperature for 72 hours. The mixture was filtered to remove a small amount of solid which was discarded and the filtrate was concentrated under reduced pressure to low volume whereupon crystals were formed. This suspension was diluted with water to approximately 250 ml and the solid was collected by filtration and recrystallized from methanol to give 3-phenyl-1,4-dihydroindeno[1,2-c]pyrazol-4-ol, m.p. 269–272° C.

Example 8 a) A mixture of indane-1,3-dione (5.85 g), piperidine (0.46 ml) and pyridine-4-carboxaldehyde (4.31 g) was stirred in IMS (40 ml) at ambient temperature for 50 minutes. The mixture was cooled in an ice-bath but no crystallization occurred. The solution was allowed to warm to ambient temperature and then the solvent was removed under reduced pressure to give a residue which was partially purified by flash column chromatography on silica using 10% industrial methylated spirit in dichloromethane followed by 20% industrial methylated spirit in dichloromethane as the mobile phases. The leading fractions were collected, combined and evaporated to give a solid which was triturated with ice-cold diethyl ether and filtered to give 2-(4-pyridylmethylene) indan-1,3-dione, m.p. 152–157° C.

b) The product from a) (0.64 g) was dissolved in a mixture of dichloromethane (5.5 ml) and methanol (5.5 ml) and the mixture was stirred at ambient temperature as 2M aqueous sodium hydroxide solution (1.36 ml) was added, followed by 100 volume aqueous hydrogen peroxide (0.55 ml). The mixture was stirred at ambient temperature for 45 minutes. Water (25 ml) and dichloromethane (25 ml) were added and the aqueous phase was separated and extracted with dichloromethane. The combined dichloromethane extracts were evaporated under reduced pressure to give 1,3-dioxo-3'-(4-pyridyl)-spiro[indan-2,2'-oxirane] in a crude form which was used directly in the next part of this example.

c) A mixture of the epoxide from b) (0.51 g), methanol (20 ml), glacial acetic acid (20 drops) and hydrazine hydrate (1 ml of a solution prepared by diluting hydrazine hydrate 1 ml to 10 ml total volume with methanol) was boiled under reflux for 18 hours. The mixture was allowed to cool and then the solvent was removed under reduced pressure. The residue was purified by flash column chromatography on silica using 5% and then 10% IMS in dichloromethane as the mobile phase. Appropriate fractions were combined and evaporated to give a solid which was triturated with diethyl ether and filtered to give 3-(4-pyridyl)indeno[1,2-c]pyrazol-4-(1H)-one, m.p.>300° C.

Example 9 a) A 1:1 mixture (by volume) of dichloromethane:methanol (1 ml) was added to 2-(4-fluorobenzylidene)-1,3-indandione (50.7 mg) in a septum sealed tube added via a Gilson 215 liquid handler, followed by aqueous 2M sodium hydroxide solution (100.5 $\mu$l) followed by 100 volumes aqueous hydrogen peroxide (41.1 $\mu$l). The resulting reaction mixture was then shaken at ambient temperature for 20 hours. Following LCMS analysis, further 100 volumes aqueous hydrogen peroxide (41.1 $\mu$l) was added, this time manually via a plastic-tipped pipette. Shaking was then continued for a further 24 hours.

The reaction mixture was equilibrated between dichloromethane (approx. 5 ml) and water (approx. 2 ml), filtering off the organic phase through an Empore® filter cartridge and washing through with dichloromethane (approx. 2 ml). The dichloromethane phase was evaporated and the residue further dried in vacuo to give 46 mg of material. The product was taken on to the next step on the basis of being the corresponding 2,3-epoxyketone.

b) n-Butanol (2 ml) was added via a Gilson 215 liquid handler to the product from a) in a septum sealed tube, followed by hydrazine hydrate as a 10% solution by volume in n-butanol (100 μl, 1.2 molar equivalents). Finally, glacial acetic acid (2 drops) was added manually by syringe. The reaction mixture was heated at 100° C. for 6 hours. The reaction mixture was evaporated to dryness and the residue was purified by chromatography on silica eluting with ethyl acetate, diluted as necessary with petroleum ether b.p. 40–60° C. Appropriate fractions were evaporated and dried in vacuo. The product was further purified by preparative HPLC to give 3-(4-fluorophenyl)indeno[1,2-c]pyrazol-4(1H)-one (1.3 mg, retention time 4.42 minutes and with MH+ corresponding to $C_{16}H_9FN_2O$=264 by LCMS). The identity of the products was confirmed by LCMS using the conditions given below.

| LC | |
|---|---|
| Column: | 5μ HYPERSIL BDS C18 (100 × 2.1 mm) |
| Mobile Phase: | 0.1% Formic Acid:MeCN (gradient-see below) |
| Conditions: | 10–100% MeCN in 8 minutes |
| (gradient) | 100% MeCN for 1 minute |
| | 100–10% MeCN in 2 minutes |
| | (Total analysis run time 11 minutes) |
| Flow Rate: | 1 ml/min |
| Wavelength Range: | 206–320 nm |
| Injection Volume: | 10 μl |

| MS | |
|---|---|
| Ionization | APcI +ve/−ve |
| Mass Range: | 150–500 m/z |
| Cone Voltage: | 20 |

The chemical structures of the compounds produced in these Examples are shown in Table II:

TABLE II

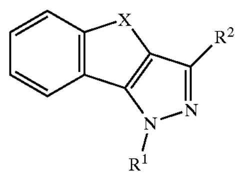

| Ex No. | X | $R^1$ | $R^2$ |
|---|---|---|---|
| 1 | CO | H | 3,4-$(OCH_3)_2$phenyl |
| 2 | CO | H | 3,4,5-$(OCH_3)_3$phenyl |
| 3 | CO | H | 4-Cl phenyl |
| 4 | CO | $CH_3$ | 4-Cl phenyl |
| 5 | CO | $CH_3$ | Phenyl |
| 6 | CHOH | H | 3,4-$(OCH_3)_2$phenyl |
| 7 | CHOH | H | Phenyl |
| 8 | CO | H | 4-pyridyl |
| 9 | CO | H | 4-F phenyl |

II. In Vitro PTK Assays

The following in vitro assays may be used to determine the level of activity and effect of the different compounds of the present invention on one or more of the PTKs. Similar assays can be designed along the same lines for other tyrosine kinases using techniques well known in the art.

A. KDR Protein Production Using Baculovirus System:

The coding sequence for the KDR intra-cellular domain (aa789–1354) was generated through PCR using cDNAs isolated from HUVEC cells. A poly-$His_6$ sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at $2\times10^6$/ml, and were infected at 0.5 plaque forming units per cell (MOI). Cells were harvested at 48 hours post infection.

B. Purification of KDR

SF-9 cells expressing $(His)_6$KDR(aa789–1354) were lysed by adding 50 ml of Triton X-100 lysis buffer (20 mM Tris, pH 8.0, 137 mM NaCl, 10% glycerol, 1% Triton X-100, 1 mM PMSF, 10 μg/ml aprotinin, 1 μg/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

C. Human Tie-2 Kinase Production and Purification

The coding sequence for the human Tie-2 intra-cellular domain (aa775–1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at $2\times10^6$/ml, and were infected at MOI of 0.5. Purification of the His-tagged kinase used in screening was analogous to that described for KDR.

D. Human Flt-1 Tyrosine Kinase Production and Purification

The baculoviral expression vector pVL1393 (Phar Mingen, Los Angeles, Calif.) was used. The nucleotide sequence encoding the kinase domain was generated through PCR using cDNA libraries isolated from HUVEC cells. A nucleotide sequence encoding poly-$His_6$ was placed 5' to the nucleotide region encoding the entire intracellular kinase domain of human Flt-1 (amino acids 786–1338). The histidine residues enabled affinity purification of the protein as a manner analogous to that for KDR (Part B.) and ZAP70 (Part F.) SF-9 insect cells were infected at a 0.5 multiplicity and harvested 48 hours post infection.

E. Lck and EGFR Tyrosine Kinase Sources

Lck or truncated forms of Lck were commercially obtained (e.g. Upstate Biotechnology Inc., Saranac Lake, N.Y. or Santa Cruz Biotechnology, Inc., Santa Cruz, Calif.) or were purified from known natural or recombinant sources using conventional methods. EGFR was purchased from Sigma (Cat # E-3641; 500 units/50 μl) and the EGF ligand was acquired from Oncogene Research Products/Calbiochem (Cat # PF011-100).

F. ZAP70 Tyrosine Kinase Production

The Baculoviral expression vector pVL 1393 (Phar Mingen, Los Angeles, Calif.) was used. A nucleotide sequence encoding poly-$His_6$ was placed 5' to the nucleotide region encoding the entire ZAP70 (amino acids 1–619). The nucleotide sequence encoding the ZAP70 coding region was generated through PCR using cDNA libraries isolated from Jurkat immortalized T-cells. The histidine residues enabled affinity purification of the protein. The LVPRGS bridge constituted a recognition sequence for proteolytic cleavage by thrombin, thereby enabling removal of the affinity tag from the enzyme. SF-9 insect cells were infected at a 0.5 multiplicity and harvested 48 hours post infection.

G. Purification of ZAP70

SF-9 cells were lysed in a buffer containing 20 mM Tris, pH 8.0, 137 mM NaCl, 10% glycerol, 1% Triton X-100, 1 mM PMSF, 1 μg/ml leupeptin, 10 μg/ml aprotinin and 1 mM sodium orthovanadate. The soluble lysate was applied to a chelating Sepharose Hi Trap column (Pharmacia) equilibrated in 50 mM HEPES, pH 7.5, 0.3 M NaCl. The fusion protein was eluted with 250 mM imidazole. The recovered enzyme was stored in buffer containing 50 mM HEPES, pH 7.5, 50 mM NaCl and 5 mM DTT.

H. Enzyme Linked Immunosorbent Assay (ELISA)

Enzyme linked immunosorbent assays (ELISA) can be used to detect and measure the presence of tyrosine kinase activity. The ELISA can be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol can be adapted for determining activity with respect to a specific RTK. For example, preferred protocols for conducting the ELISA experiments for KDR is provided below. Adaptation of these protocols for determining a compound's activity for other members of the RTK family, as well as non-receptor tyrosine kinases, are well within the abilities of those in the art. For purposes of determining inhibitor selectivity, a universal PTK substrate (e.g., random copolymer of poly ($Glu_4Tyr$) 20,000–50,000 MW) was employed together with ATP (typically 5 μM) at concentrations approximately twice the apparent $K_m$ in the assay.

KDR IN VITRO ELISA

The following procedure was used to assay the inhibitory effect of compounds of this invention on KDR tyrosine kinase activity:

Buffers and Solutions:

1. PGT: Poly (Glu,Tyr) 4:1

Store powder at −20° C. Dissolve powder in phosphate buffered saline (PBS) for 50 mg/ml solution. Store 1 ml aliquots at −20° C. When making plates dilute to 250 μg/ml in Gibco PBS.

2. Reaction Buffer:

100 mM Hepes, 20 mM $MgCl_2$, 4 mM $MnCl_2$, 5 mM DTT, 0.02%BSA, 200 μM $NaVO_4$, ph 7.10

3. ATP:

Store aliquots of 100 mM at −20° C. Dilute to 20 μM in water.

4. Washing Buffer:

PBS with 0.1% Tween 20

5. Antibody Diluting Buffer:

0.1% bovine serum albumin (BSA) in PBS

6. TMB Substrate:

Mix TMB substrate and Peroxide solutions 9:1 just before use or use K-Blue Substrate from Neogen 7. Stop Solution:

1M Phosphoric Acid

Procedure

1. Plate Preparation:

Dilute PGT stock (50 mg/ml, frozen) in PBS to a 250 μg/ml. Add 125 μl per well of Corning modified flat bottom high affinity ELISA plates (Corning #25805-96). Add 125 μl PBS to blank wells. Cover with sealing tape and incubate overnight 37° C. Wash 1× with 250 μl washing buffer and dry for about 2 hrs in 37° C. dry incubator.

Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 μl, e.g. for KDR make to 1 ng/μl for a total of 50 ng per well in the reactions. Store on ice.

Make 4× ATP solution to 20 μM from 100 mM stock in water. Store on ice

Add 50 μl of the enzyme solution per well

Add 25 μl 4× inhibitor

Add 251 μl 4× ATP for inhibitor assay

Incubate for 10 minutes at room temperature

Stop reaction by adding 50 μL 0.05N HCl per well

Wash plate

**Final Concentrations for Reaction:

ATP: 5 μM

5% DMSO

3. Antibody Binding

Dilute 1 mg/ml aliquot of PY20-HRP (Pierce) antibody to 50 ng/ml in 0.1% BSA in PBS by a 2 step dilution (100×, then 200×)

Add 100 μl Ab per well. Incubate 1 hr at room temp. Incubate 1 hr at 4C.

Wash 4× plate

4. Color Reaction

Prepare TMB substrate and add 100 μl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

Analogous assay conditions were used for Flt-1, Tie-2, EGFR and ZAP70. For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

PKC Kinase Source

The catalytic subunit of PKC may be obtained commercially (Calbiochem).

PKC Kinase Assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10 mM $MgCl_2$, 2 mM DTT, 1 mM EGTA, 100 μM ATP, 8 μM peptide, 5% DMSO and $^{33}P$ ATP (8Ci/mM). Compound and enzyme were mixed in the reaction vessel and the reaction initiated by addition of the ATP and substrate mixture. Following termination of the reaction by the addition of 10 μL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Results

The following inhibitory concentrations for representative compounds were obtained:

| Compound of Formula I where: | KDR ELISA $IC_{50}$ |
|---|---|
| X is carbonyl, $R^1$ is hydrogen and $R^2$ is phenyl | 0.15 $\mu$M |
| X is carbonyl, $R^1$ is hydrogen and $R^2$ is 4-methylphenyl | 2.6 $\mu$M |
| X is carbonyl, $R^1$ is hydrogen and $R^2$ is 4-methoxyphenyl | 1.5 $\mu$M |
| O, $CH_3$, N, N | >100 $\mu$M |
| N, N, N, HN | >100 $\mu$M |

These results demonstrate that compounds of the present invention have notable inhibitory activity for KDR tyrosine kinase, particularly when compared to the lack of inhibitory activity for KDR tyrosine kinase by compounds outside the scope of the present invention.

III. Cellular RTK Assays

The following cellular assays may be used to determine the level of activity and effect of the different compounds of the present invention on one or more of the RTKs. Similar assays can be designed along the same lines for other tyrosine kinases using techniques well known in the art.

A. VEGF-Induced KDR Phosphorylation in Human Umbilical Vein Cells (HUVEC) as Measured by Western Blots.

1. HUVEC cells (from pooled donors) were purchased from Clonetics (San Diego, Calif.) and cultured according to the manufacturer directions. Only early passages (3–8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5–1.0\times10^5$ cells/well in each well of 6-well cluster plates (Costar; Cambridge, Mass.).

3. 3–4 days after seeding, plates were 90–100% confluent. Medium was removed from all the wells, cells were rinsed with 5–10 ml of PBS and incubated 18–24 h with 5 ml of EBM base media with no supplements added (i.e., serum starvation).

4. Serial dilutions of inhibitors were added in 1 ml of EBM media (25 uM, 5 uM, or 1 uM final concentration) to cells and incubated for one hour at 37° C. Human recombinant $VEGF_{(165)}$ (R&D Systems) was then added to all the wells in 2 ml of EBM medium at a final concentration of 50 ng/ml and incubated at 37° C. for 10 minutes. Control cells untreated or treated with VEGF only were used to assess background phosphorylation and induction by VEGF.

5. All wells were then rinsed with 5–10 ml of cold PBS containing 1 mM Sodium Orthovanadate (Sigma) and cells were lysed and scraped in 200 $\mu$l of RIPA buffer (50 mM Tris-HCl pH7,150 mM NaCl,1% NP-40, 0.25% sodium deoxycholate, 1 mM EDTA) containing protease inhibitors (PMSF 1 mM, Aprotinin 1 $\mu$g/ml, Pepstatin 1 $\mu$g/ml, Leupeptin 1 $\mu$g/ml, Na Vanadate 1 mM, Na Fluoride 1 mM) and 1 $\mu$g/ml of DNase (all chemicals from Sigma Chemical Company, St. Louis, Mo.). The lysate was spun at 14,000 rpm for 30 min, to eliminate nuclei.

6. Equal amounts of proteins were then precipitated by addition of cold (−20 C) Ethanol (2 volumes) for a minimum of 1 hour or a maximum of overnight. Pellets were reconstituted in Laemli sample buffer containing 5% β-mercaptoethanol (BioRad; Hercules, Calif.) and boiled for 5 min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology;, Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated $F(ab)_2$ of goat anti-rabbit or goat-anti-mouse IgG the bands were visualized using the emission chemiluminescience (ECL) system (Amersham Life Sciences, Arlington Height, Ill.).

For example, when X is carbonyl, $R^1$ is hydrogen and $R^2$ is phenyl in a compound of Formula I, the cellular $IC_{50}$ according to this method is 3 $\mu$M.

B. HUVEC Mitogenesis Assay

Human umbilical vein endothelial cells (HUVEC) were cultured in EGM-Complete Media (endothelial growth media supplemented with 10% FBS, hydrocortisone, epidermal growth factor and bovine brain extract as per the supplier's directions). Cells, media and supplements were purchased from Clonetics (San Diego, Calif.). The HUVEC Mitogenesis Assay was used to measure inhibition of mitogenesis induced by VEGF, FGF or Complete Media. Cells were harvested by trypsinization, washed once and suspended in Complete Media (CM) at a concentration of 5,000 cells/0.15 ml. Cells were seeded into 96-well plates at 5,000 cells/well and incubated at 37° C. for 24 hours. Cells were washed once with serum-free media (SFM) and incubated under serum-free conditions for 24 hours. Non-serum starved control wells were cultured with CM during this period. Test compounds were prepared as 10 mM stock solutions in DMSO, diluted in SFM and added to wells over a concentration range (0.005–50 $\mu$M final concentration). Cells were incubated for 1 hour prior to addition of 50 ng/ml VEGF or FGF (R & D Systems, Minneapolis, Minn.). Complete media stimulated wells received the test compound and stimulus simultaneously. After 5 hours of incubation, 0.5 Ci/well of tritiated thymidine (Amersham) was added and the cells were incubated overnight. The assay was stopped by freezing plates at −20° C. for 24 hours. Plates were harvested onto filter mats with a Tomtec Harvester and counted with a Betaplate liquid scintillation counter (Wallac).

For example, when X is carbonyl, $R^1$ is hydrogen and $R^2$ is phenyl in a compound of Formula I, the HUVEC mitogenesis $IC_{50}$ according to this method is <0.10 $\mu$M.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of inhibiting tyrosine kinase activity comprising the administration of a compound represented by the formula:

I

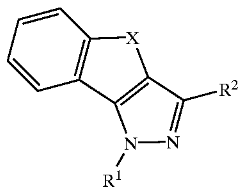

wherein:

X is a carbonyl;

$R^1$ is a hydrogen; and $R^2$ is a pyridyl to said tyrosine kinase in sufficient concentration to inhibit the enzyme activity of said tyrosine kinase.

2. The method of claim 1 wherein said compound is in an enantiomeric form, a tautomeric form, is in a mixture with one or more other said compounds, or is both in an enantiomeric form and in a mixture with one or more other said compounds.

3. The method of claim 1 wherein said tyrosine kinase is either a receptor tyrosine kinase or a non-receptor tyrosine kinase.

4. The method of claim 3 wherein said tyrosine kinase is selected from the group consisting of KDR, flt-1, TIE-2, Lck, Src, fyn, and yes.

5. The method of claim 1 wherein the activity of said tyrosine kinase affects angiogenesis.

6. The method of claim 5 wherein the inhibition of said tyrosine kinase is anti-angiogenic.

7. The method of claim 6 wherein said inhibition of said tyrosine kinase inhibits the progression of the disease state selected from the group consisting of arthritis, atherosclerosis, psoriasis, hemangioma, myocardial angiogenesis, coronary and cerebral collateral vascularization, ischemic limb angiogenesis, corneal disease, rubeosis, neovascular glaucoma, macular degeneration, wound healing peptic ulcer Helicobacter related diseases, fractures, diabetic retinopathy and cat scratch fever.

8. The method of claim 1 wherein the activity of said tyrosine kinase affects vascular hyperpermeability.

9. The method of claim 1 wherein said compound is represented by the formula:

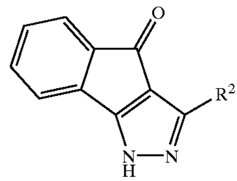

wherein $R^2$ is selected from the group consisting of 3-pyridyl and 4-pyridyl.

10. The method of claim 1 wherein said compound is represented by the formula:

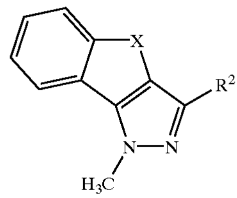

wherein $R^2$ and X are respectively 3-pyridyl and CO.

11. The method of claim 1 wherein X is a carbonyl and $R^1$ is a hydrogen, wherein the inhibition of said tyrosine activity is associated with anti-fertility or abortifacient effects.

* * * * *